(12) United States Patent  
Hull, Jr. et al.

(10) Patent No.: US 6,299,573 B1
(45) Date of Patent: Oct. 9, 2001

(54) DOMED COMPRESSED TAMPONS

(75) Inventors: Raymond J. Hull, Jr., Hampton; Gerd R. Rex, Somerset; Wilfried Baer, Princeton, all of NJ (US); Masaki Kasahara, Takahara; Toshio Sonoda, Mihara, both of (JP)

(73) Assignee: eil-PPC, Inc., lman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/369,572

(22) Filed: Aug. 6, 1999

Related U.S. Application Data

(62) Division of application No. 08/829,369, filed on Mar. 31, 1997, now Pat. No. 6,003,216.

(51) Int. Cl.$^7$ ........................................................ B31B 1/00
(52) U.S. Cl. ........................... 493/464; 53/436; 604/904; 28/118
(58) Field of Search ..................................... 493/464, 967; 53/436, 438, 523, 529; 28/118, 119, 120; 604/904, 328, 330, 14, 358, 379

(56) References Cited

U.S. PATENT DOCUMENTS

| | | |
|---|---|---|
| 2,798,260 | 7/1957 | Niepmann et al. . |
| 3,422,496 | 1/1969 | Wolff et al. . |
| 3,433,225 * | 3/1969 | Voss et al. ............................. 604/14 |
| 3,710,420 * | 1/1973 | Yamauchi ............................. 28/120 |
| 3,732,804 | 5/1973 | Moller . |
| 3,738,364 * | 6/1973 | Brien et al. ............................ 28/120 |
| 3,845,520 | 11/1974 | Simon . |
| 3,866,737 | 2/1975 | Simon . |
| 4,019,226 | 4/1977 | Yamauchi et al. . |
| 4,081,884 * | 4/1978 | Johst et al. ............................. 28/119 |
| 4,109,354 | 8/1978 | Ronc . |
| 4,351,339 * | 9/1982 | Sneider ................................. 604/904 |
| 4,453,296 * | 6/1984 | Friese .................................... 28/119 |
| 4,498,218 | 2/1985 | Friese . |
| 4,498,899 | 2/1985 | Gross . |
| 5,149,332 * | 9/1992 | Walton et al. ........................ 604/379 |
| 5,160,031 | 11/1992 | Palisin, Jr. et al. . |
| 5,171,235 * | 12/1992 | Theis et al. .......................... 604/904 |
| 5,273,521 | 12/1993 | Peiler et al. . |
| 5,660,029 | 8/1997 | King . |
| 5,693,009 * | 12/1997 | Fox et al. ............................. 604/14 |
| 5,911,712 | 6/1999 | Leutwyler et al. . |

FOREIGN PATENT DOCUMENTS 1336702    12/1963   (FR) .

* cited by examiner

Primary Examiner—Peter Vo
Assistant Examiner—Louis K. Huynh

(57) ABSTRACT

An improved apparatus and method compresses a cylindrical blank into a tampon which is dimensionally stable and which is provided with a domed insertion end. A cylindrical blank is radially compressed and then introduced into a cylindrical axial compression chamber. The blank is then subjected to an extreme axial overcompression. The closed insertion end of the compression chamber has a bore formed therethrough. The bore is generally coaxial and is adapted to accept a reciprocating ejection ram having a ram surface facing into the chamber. When the ram is seated in the first position, the ram surface and the insertion end wall of the compression chamber together form a smooth doming surface. The bore periphery is of a smaller diameter than the chamber and hence radially spaced from the side walls of the chamber, and the ram has sufficient clearance to move through the chamber and eject the tampon without interference from the walls of the chamber.

2 Claims, 4 Drawing Sheets

FIG. 1
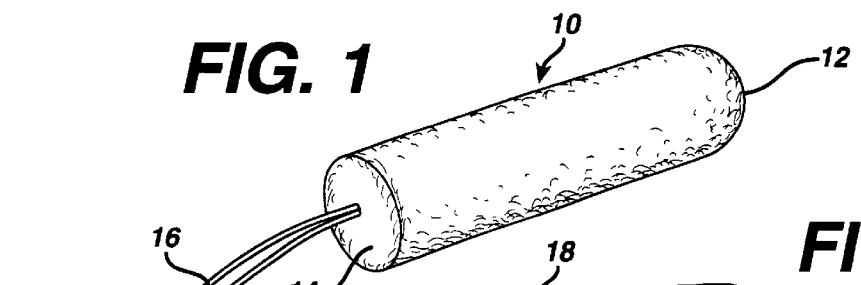
FIG. 2
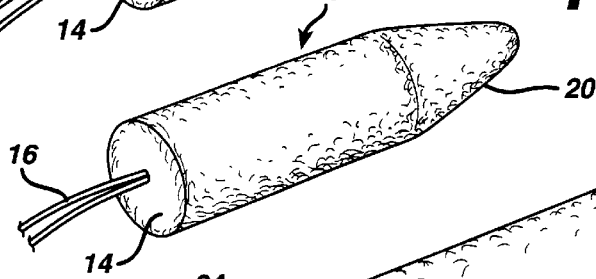
FIG. 3
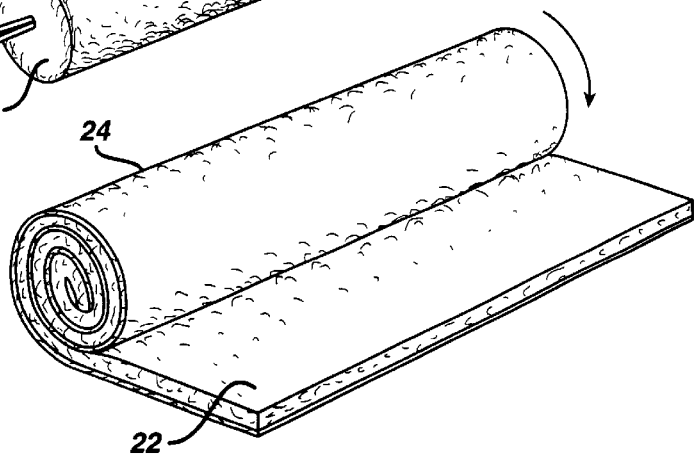
FIG. 4a   FIG. 4b   FIG. 4c
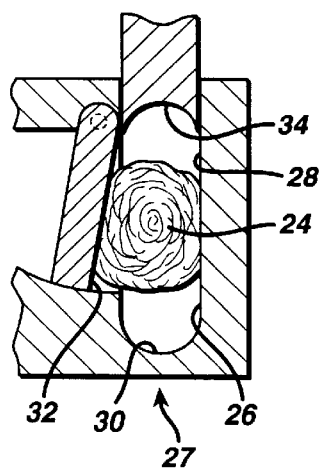 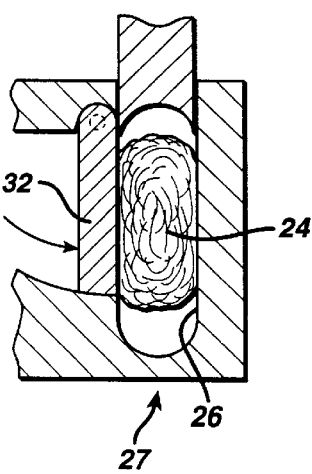 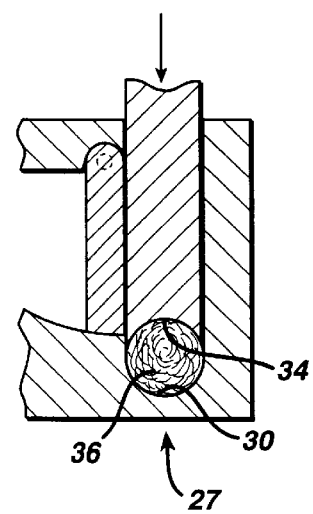

DOMED COMPRESSED TAMPONS

This is a divisional of prior application Ser. No. 08/829,369, filed Mar. 31, 1997, now U.S. Pat. No. 6,003,216.

BACKGROUND OF THE INVENTION

This invention concerns apparatus and methods for providing dimensionally stable absorbent bodies which comprise cellulose fibers and, in particular, concerns providing such bodies compressed into cylindrical tampons having a rounded or domed tip. Specifically, this invention provides methods and apparatus for manufacturing dimensionally stabilized tampons with a domed tip having a smooth surface.

Absorbent, cylindrical tampons are now widely used for a number of absorbent purposes in the medical and dental field but are primarily used in the field of feminine hygiene as catamenial tampons. In this latter field, there are two basic types: digitally inserted tampons, inserted with the fingers, and applicator tampons inserted with the aid of an applicator. Both types are usually made by folding or rolling a loosely associated, generally rectangular strip of absorbent material, usually fibrous and cellulosic in nature, into a blank and then compressing the blank into a cylindrically shaped product. In the case of digital tampons, the product is then wrapped and packaged and, in the case applicator tampons, the product is first inserted into the applicator and then wrapped and packaged.

In both instances it is highly desirable that the tampon maintains its final compressed shape and presents a smooth outer surface at the dome whereby both the removal from the applicator and/or packaging and the insertion into the vagina are facilitated. To this end, the art has provided various suggestions for attaining shape stability and surface smoothness of the dome tip. In U.S. Pat. No. 4,081,884 for example, it has been suggested that a tampon blank be first radially compressed and then axially compressed and, while in the axially compressed state, heated to impart a set to the compressed body. The axial compression is applied to the extent that the axially compressed tampon is about 90 to about 98% of the desired length of the tampon in its final state. Owing to the heat setting technique described therein, the tampon is said to "grow" only moderately i.e. 2–10%, based on the final length. While this technique does indeed produce a relatively dimensionally stable tampon, unfortunately the required heating step entails expensive equipment and is particularly difficult to carry out at the high production speeds (of up to fifteen hundred tampons per minute) required for practical commercialization.

The art has also made suggestions with respect to presenting a smooth forward or insertion end for the tampon and, in particular for presenting a tapered, domed, or hemispherical end for a tampon to facilitate insertion. Such a suggestion may be found in U.S. Pat. No. 3,738,364 wherein a ram having a recess designed to impart a tapered shaped to a tampon blank is described. Most recently, in European Patent Application 94/102244.4 filed on Feb. 14, 1994, there is described a tampon blank which is axially compressed in a cylinder between two rams with the insertion end ram having a cup like recess to impart a hemispherical shape to the insertion end of a tampon. Such a system is found to work well for a moderate degree of axial compression. On the other hand, as will be described in greater detail herein drawbacks are inherent in such systems. This is particularly true in seeking to obtain dimensional stability without resorting to a heat setting step and at the same time attempting to dome the insertion end of the tampon.

SUMMARY OF THE INVENTION

This invention therefore concerns providing an improved apparatus and method for compressing a cylindrical blank into a tampon which is dimensionally stable and is provided with a domed insertion end. Specifically, the invention comprises introducing a cylindrical blank into a cylindrical axial compression chamber having an insertion end, an opposed withdrawal end and cylindrical side walls therebetween. The withdrawal end of the chamber is open and adapted for the introducing the cylindrical blank into the chamber and for accepting a reciprocating compression ram. The compression ram is adapted to axially reciprocate into the chamber and exert axial compression force against the withdrawal end of the so introduced cylindrical blank. The insertion end of the chamber presents an immovable closed insertion end wall to the cylindrical blank when it is introduced into the chamber. Upon introducing the blank into the chamber and urging the axial compression ram toward the insertion end to axially compress the blank therebetween, the insertion end of the blank is forced against the closed inner surface of the insertion end of the chamber and takes the shape of this inner surface; preferably, a smooth surfaced dome, e.g., a hemispherical shape.

In accordance with this invention, shape stability is achieved, not as in the prior art by slight overcompression and recovery in conjunction with heat setting, but instead, by an extreme axial overcompression step. In the axial compression step of an embodiment of this invention the blank is pressed from its original length to a length ranging from about 15–30% of its original length. Blank is then allowed to recover to a finished compressed tampon with the recovery length ranging from about 50–80% of the original blank length. Blank length is chosen to produce a finished tampon which has the desired finished length, e.g., about 45 millimeters.

The high degree of axial overcompression has been found to result in a dimensionally stable tampon without the need for heat setting. While the precise reasons for the remarkable stability of the tampon is not entirely known, it is believed to be the result of circular pleats forming on the cylindrical surface of the blank during the compression step. These pleats tend to fold over the cylindrical surface. When constrained from opening, as when the finished tampon is packaged and/or placed in an applicator, the pleats retard axial growth. It has been discovered however that the high degree of compression in combination with conventional doming techniques and apparatus, does not result in a smooth surfaced domed insertion end. Accordingly, the closed insertion end of the compression chamber is, in accordance with this invention, uniquely designed to insure such smooth surface. Specifically, the closed end wall of the chamber comprises a bore therethrough. The bore is generally coaxial with the chamber and has a periphery, at the insertion end wall, having a smaller diameter than that of the cylindrical compression chamber. The bore is adapted to accept a reciprocating ejection ram having a ram surface facing into the chamber. The ram may be seated, in a first position, with the ram surface contiguous with the insertion end wall. Further, the ram may be axially reciprocated out of such first position, through the bore and through the compression chamber to eject the axially compressed blank. When the ram is seated in the first position, the ram surface and the insertion end wall of the compression chamber together form a smooth doming surface for imparting a smooth surfaced dome to the insertion end of the blank when the blank is compressed by the action of the compression ram. The smooth doming surface may be accomplished as a result of having the ram closely fitted to the bore at the periphery so as to present essentially no gap between the bore periphery and the ram surface. The dome shape may be imparted by machining the insertion end wall with the seated ram in place, thereby obtaining a continuous smooth doming surface. Because the ram is closely fitted within the bore, no ridges are formed on the insertion end of the tampon, notwithstanding the high degree of axially compression. Notwithstanding the tight fit of the ram within the bore, because the bore periphery is of a smaller diameter than the chamber and hence radially spaced from the side walls of the chamber, the ram has sufficient clearance to move through the chamber and eject the tampon without interference from the walls of the chamber.

BRIEF DESCRIPTION OF THE DRAWINGS

FIG. 1 is a perspective view of a domed tampon of this invention having a generally a hemispherical insertion end;

FIG. 2 is a perspective view of a domed tampon of this invention having a generally tapered end;

FIG. 3 schematically illustrates, in perspective view, a method for producing a blank for compression in accordance with this invention;

FIG. 4a schematically illustrates, in cross-sectional end view a first step in the method for radially compressing a blank;

FIG. 4b schematically illustrates, in cross-sectional end view a second step in the method for radially compressing the blank;

FIG. 4c schematically illustrates, in cross-sectional end view a third step in the method for radially compressing the blank;

FIG. 6b is a enlarged fragmented view of the insertion end of the apparatus shown in FIG. 6a;

DETAILED DESCRIPTION OF THE INVENTION

Figure 5A:
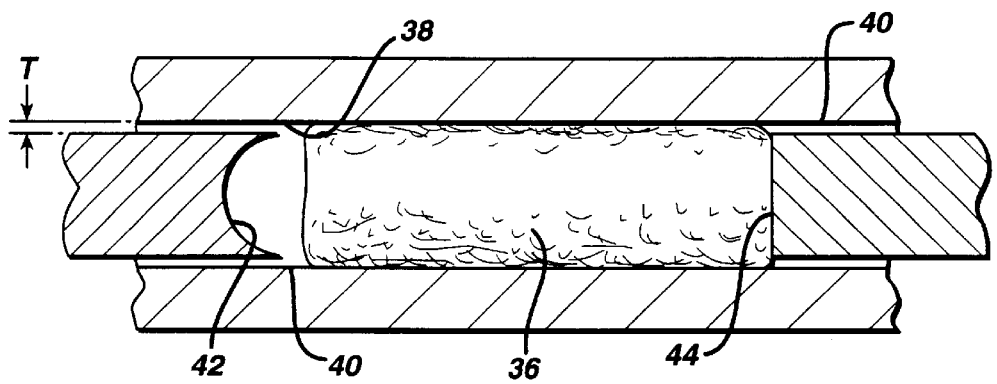
FIG. 5a schematically illustrates, in longitudinal cross-sectional view, a first step in a method of axially compressing and doming a tampon blank employing, in part, the teachings of the prior art.

Referring now to the drawings, FIG. 1 illustrates a domed tampon 10 in its final desired shape, exhibiting a smooth, hemispherical insertion end 12 and a rear or withdrawal end 14. A withdrawal string 16 is affixed to the withdrawal end 14 for removal of the tampon after use. FIG. 2 illustrates an alternative design for a tampon 18 characterized by a smooth tapered insertion end 20. It will be understood that the descriptions hereinafter will primarily be focused on the embodiment of a tampon illustrated by FIG. 1 but will be equally applicable to a tampon such as that illustrated in FIG. 2 as well as other such variations in shape or proportions.

FIG. 3 schematically illustrates one method for preparing an uncompressed blank for manufacturing a tampon illustrated in FIGS. 1 and 2. A rectangular pad 22 of absorbent material is rolled into a spiral configuration to form a generally cylindrical blank 24. The pad 22 may comprise any of a number of absorbent materials or combinations thereof. Generally, however, such a pad comprises fibrous cellulosic materials and, in particular, cellulosic fibers of, for example, wood pulp, cotton or rayon. Other materials, both fibrous and nonfibrous (e.g., granulated, powdered, foamed, and the like) may be incorporated to increase absorbency or provide other functions such as odor control or antimicrobial activity. When the absorbent material is primarily fibrous, rectangular pads of these fibers will generally maintain sufficient integrity to be processed into blanks. Such pads will have, for example, a density ranging from about 0.04 to about 0.07 grams/cc. On the other hand where materials are in powdered form, they may be combined with fibers to form a pad or may be held together by means of binders or the like. One possibility, for example, is to form a nonwoven fabric from a combination of fibers and powders and use the fabric as an absorbent. It will be understood that a pad rolled into a spiral blank is not the only form of a starting blank useable in connection with the teachings of this invention. For example, absorbent material can be enveloped by a generally cylindrical shaped sack of fluid pervious nonwoven fabric and may be used in this form as well. Additionally, the blank may be provided with a cover of an apertured film or of woven or non-woven fibers such as polyester, polyethylene, polypropylene, rayon, or the like.

Irrespective of the materials of construction or the methods for providing the blank, the blank has a length in excess of the desired length for the finished tampon and a diameter in excess of the desired diameter of the finished tampon. Preferably, it is first radially compressed. Several methods for such radial compression are known in the art. For example, U.S. Pat. Nos. 2,798,260; 3,422,496; 3,845,520; and 4,081,884 all illustrate radial compression. FIGS. 4a–4c schematically illustrate a radial compression scheme employable in connection with this invention. As viewed in these Figures, the rolled blank 24 is shown in cross-sectional end view. In FIG. 4a, the blank has been inserted into the radial compression chamber 26 of a tampon apparatus 27. The chamber 26 has a length (out of the plane of the drawing) of at least that of the longitudinal length of the blank 24. In the open position illustrated in FIG. 4a, the chamber comprises an immovable flat side wall 28 and an immovable concave inwardly shaped end wall 30, a pivotal flat side wall 32 and a reciprocating concave inwardly shaped end wall 34. As illustrated in FIG. 4b, upon insertion of the blank 24 into the chamber 26, the pivotal flat side wall 32 is pivoted against the blank to be parallel to the opposed immovable flat side wall 26 and to impart a first radial compression to the blank. Then, as illustrated in FIG. 4c, the reciprocating concave inwardly shaped end wall 34 is reciprocated toward the immovable concave inwardly shaped end wall 30 to further radially compress the blank therebetween and impart thereto a cylindrical shape.

Figure 5B:
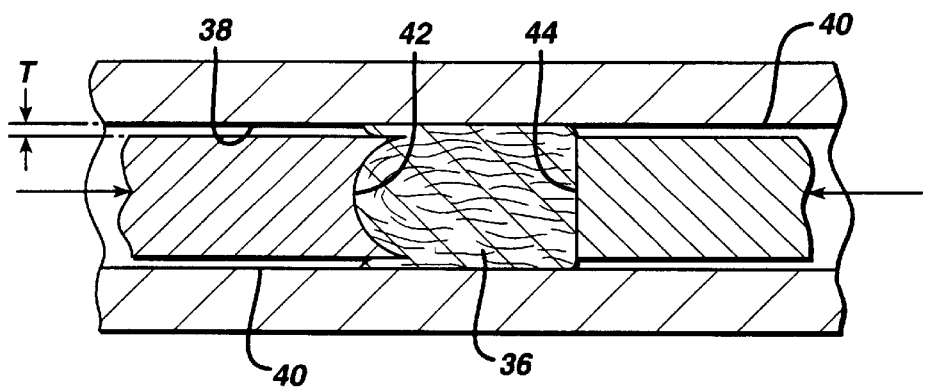
FIG. 5b schematically illustrates, in longitudinal cross-sectional view, a second step in the method of axially compressing and doming a tampon blank employing, in part, the teachings of the prior art.
Figure 5C:
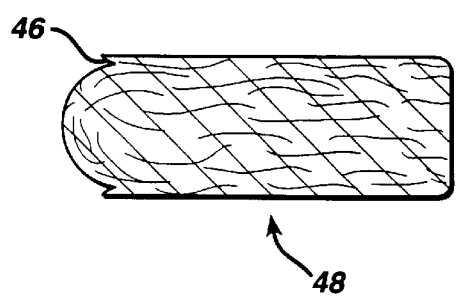
FIG. 5c illustrates the compressed tampon resulting from the methods of FIGS. 5a and b.

The now radially compressed blank 36 is next transferred to an axial compression chamber. As aforementioned, axial compression and apparatus for carrying out such compression are known in the art and are illustrated, for example, in U.S. Pat. Nos. 3,738,364 and 4,081,884. FIGS. 5a–c, schematically represent such prior art methods and devices. Referring to FIG. 5a, the prior art axial compression chamber 38 is illustrated as having a cylindrical chamber formed of immovable side walls 40, a reciprocating insertion end wall 42 and a reciprocating withdrawal end wall 44. The inwardly facing surface of insertion end wall 42 is provided with a spherically shaped recess to provide the dome tip of the insertion end of the tampon. Generally, the radially compressed blank 36 may be transferred from the radial compression chamber 26 and into the axial compression chamber by axially aligning the two chambers and pushing the radially compressed blank 36 out of the radial compression chamber and into the axial compression chamber. This pushing may be accomplished, for example, by use of the reciprocating withdrawal end wall 44 which can be used to urge the blank out through the radial compression chamber and into the axial compression chamber. Alternatively, other pushing means (not shown) may be employed and, in fact, an intermediate transfer or carrying chamber may be employed in transferring or carrying the radially compressed blank to the axial compression chamber.

Irrespective of the means of transfer, FIG. 5a illustrates the radially compressed blank 36 residing within the prior art axial compression chamber prior to any axial compression. Referring to FIG. 5b, the axial compression is accomplished by urging the reciprocating end walls towards each other thereby compressing the blank 36 therebetween and imparting a hemispherical dome shape to the insertion end of the blank. The compression may be accomplished by moving both reciprocating ends, or instead, by fixing one end, e.g., the insertion end, and moving the other end toward the fixed end. Upon completion of the compression, the insertion wall is reciprocated to eject the finished tampon.

The above described axial compression methods and apparatus have been quite satisfactory in providing domed tampons when, as is employed in the methods of U.S. Pat. No. 4,081,884, only relatively moderately compression is applied. For example, in the aforementioned patent, the compression is sufficient to compress the tampon blank to a length of about 90–98% of the final desired length of the tampon. To prevent "growth" and to stabilize the tampons length, when employing such moderate compression it is necessary to also apply a heat set and such a method has proved to be commercially impractical.

In accordance with the teachings of this invention, the axial compression is employed to provide a stable finished tampon length without the need for a heat setting step. This is accomplished, as taught herein, by a far more severe axial compression than has been proposed heretofore. Specifically, the blank is pressed from its original length to a length ranging from about 15–30% of its original length. By this means, growth is limited to about 65% of the blank's original length. The length of the original blank is of course chosen so as to reach the desired length after this extreme compression and regrowth process. For example, to produce a tampon of 45 mm in length, the axial compression is carried out on a blank of 70 mm in length axially compressed to 16 mm (23% of the original blank length) and then allowed to "grow" to 45 mm (64% of the original blank length).

The prior art methods and apparatus as described in FIGS. 5a and 5b have proven to be inappropriate for the methods of this invention. Specifically, referring to FIGS. 5a and 5b it should be noted that in order to reciprocate the end walls 42 and 44, it is necessary to provide a gap or tolerance fit (shown as dimension T) between the side walls 40 and the end walls 42 and 44. When axially compressing the blank under moderate conditions, this has not proven to be an adverse factor in the process. On the other hand, when employing the teachings of this invention and compressing under the severe conditions set out herein, we have found that the prior art methods and apparatus produce disastrous results. Under the severe compressing conditions, fibers from the blank are forced into the gap producing the product illustrated in FIG. 5c. In contrast to the desired smooth surface, a circular ridge 46 is formed about the domed end of the finished tampon 48, clearly an intolerable result.

Figure 6A:
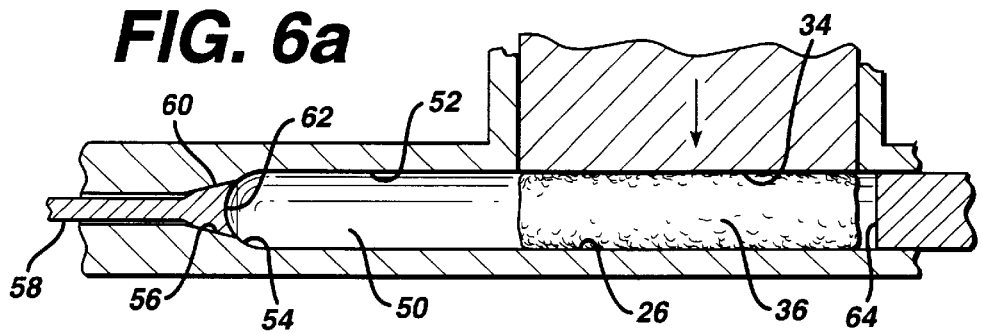
FIG. 6a schematically illustrates, in longitudinal cross-sectional view, the apparatus and the first step in a method incorporating the teachings of this invention for axially compressing and doming a tampon blank.
Figure 6B:
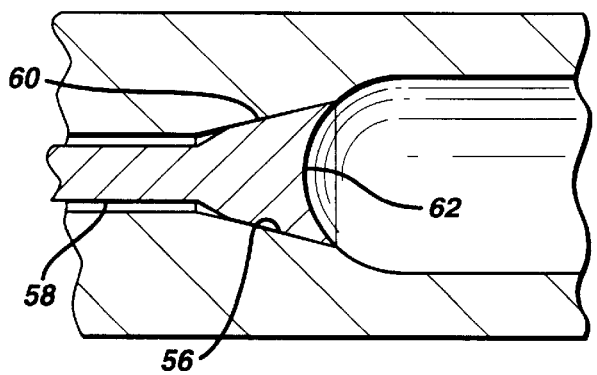

Referring now to FIGS. 6a–6d, illustrated therein is a method and apparatus for employing the teachings of this invention and avoiding the aforementioned drawbacks of the prior art. Illustrated in FIG. 6a is the radially compressed blank 36, in longitudinal cross-section as it resides in the radial compression chamber 26 just after end wall 34 has been reciprocated (in the direction of the arrow) to complete the radial compression. Immediately adjacent radial compression chamber 26 and axially aligned therewith, is axial compression chamber 50. Axial compression chamber 50 is comprised of cylindrical side walls 52 and an immovable insertion end wall 54. As best seen in FIG. 6b, insertion end wall 54 is machined or otherwise fabricated to have an inwardly facing concave hemispherical shape so as to impart a hemispherical dome to the insertion end of the finished tampon. A bore 56 is provided through end wall 54 and is coaxial with the axial compression chamber 50 but is of a smaller diameter than the chamber 50. Fitted into the bore 56 is a reciprocating ejection ram 58 having a ram head 60. The inwardly facing surface 62 of the ram head 60 is machined or otherwise fabricated to present, together with the insertion end wall 54, a smooth inwardly facing concave hemispherical surface for doming the tampon blank 36. The ram head is tightly fitted in the bore at the periphery of the bore 56 at the insertion end 54.

Figure 6C:
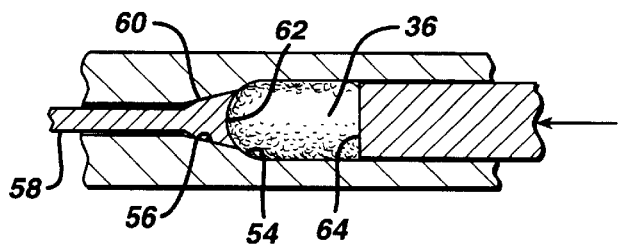
FIG. 6c schematically illustrates, in longitudinal cross-sectional view, a second step in the method of this invention.

Reciprocating withdrawal end ram 64 is provided coaxial to both compression chambers 36 and 50. In operation, reciprocating withdrawal end ram 64 is reciprocated against the withdrawal end of radially compressed blank 36 to urge blank 36 coaxially out of radial compression chamber 26 and into axial compression chamber 50. As illustrated in FIG. 6c, ram 64 is then further or continuously reciprocated towards insertion end 54 of chamber 50 to axially compress blank 36. The hemispherical dome shape desired is imparted on the insertion end of the blank by the concave inwardly hemispherical shaped surface comprising the inwardly facing surfaces of the insertion end 54 and the face 62 of the ejection ram head 60. Because there is essentially no gap between the face 62 and the periphery of the bore 56 at the end wall 54, no fibers of the blank can be trapped to create the undesirable ridge found in the prior art; this is so notwithstanding the extreme compression applied to the blank in accordance with the teachings herein.

Figure 6D:
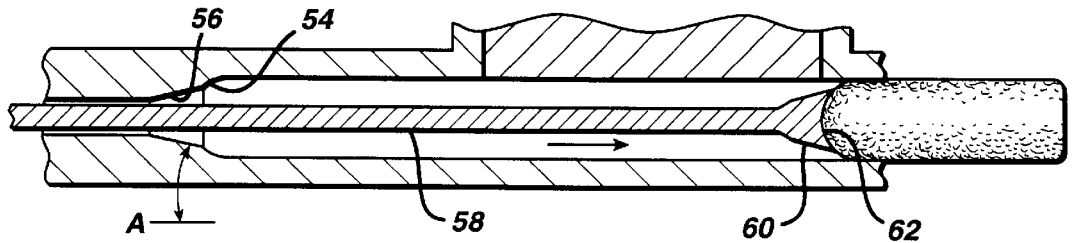
FIG. 6d schematically illustrates, in longitudinal cross sectional view, a third step in the method of this invention.

As illustrated in FIG. 6d, notwithstanding the lack of a gap, the ejection ram can now be reciprocated smoothly towards the withdrawal end of the axial chamber to eject the now axially compressed tampon. The need for the gap at the end wall has been primarily avoided in that the ram head and of course the main shaft of the ram is of a substantially smaller diameter then the axial compression chamber and hence experiences no frictional resistance as the ram freely reciprocates through the axial compression chamber and, in the example illustrated, through the radial compression chamber. Smooth passage of the tight fitting ram head is further facilitated by providing the bore 56 and the ram 60 with a taper i.e., with a diameter which decreases in a direction axially away from the insertion in wall 54. In this manner, the ram makes essentially only line contact with the end wall at the periphery of the bore just prior to reciprocating the ejection ram 58. Thereafter, no frictional contact exists, thus essentially obviating the need for a gap. An additional advantage of the taper is that the ram will thus be better supported to resist the forces of the extreme compression step of this invention. By virtue of the taper, force components are created against the side walls of the bore, adding to the resistance of the ram. The taper should be such as to provide an included angle (angle A in FIG. 6d) of at least ten degrees.

The diameter of the face 62 of the ram head 60 is substantially smaller than that of the chamber 50 and need only be large enough to ensure stable ejection of the axially compressed blank without damage thereto. Preferably such diameter is from about 40% to about 95% of the chamber diameter and still more preferably from about 70% to about 90%. If the diameter is too large, in addition to creating friction, the tapered ram head will from the geometry of the design, be required to be too sharp and, in the extreme create a weakened knife edge at the periphery. If the diameter is too small, the head will be unstable and may also damage the tampon.

Figure 7:
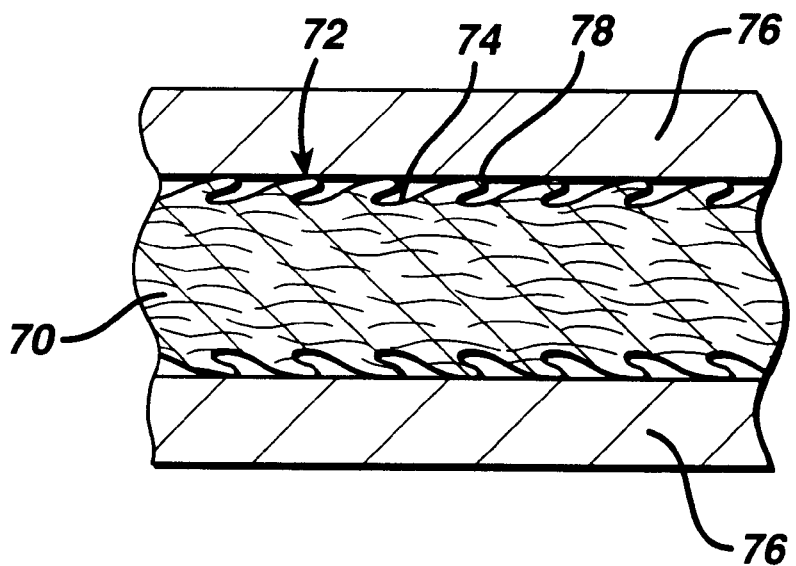
FIG. 7 schematically illustrates, in longitudinal, fragmented, cross-sectional view, a pleated axially compressed blank, constrained by cylindrical walls.

Referring now to FIG. 7, illustrated there in schematic, fragmented, cross-sectional view, is an axially compressed blank 70. In accordance with the teachings of the invention, the axially compressed blank 70 has been compressed to a degree that circular pleats 72 have been formed on the cylindrical surface of the compressed blank. These pleats are formed by the action of friction between the constraining walls 76 and the blank when walls 76 represent the walls of the compression chamber. Moreover, the axial compression is applied to the extent that the pleats 72 fold over toward the adjacent portion 74 of the cylindrical wall of the blank in the direction toward the withdrawal end of the blank. It is believed that this configuration provides axial direction stability. It is suggested that this comes about when such a compressed pleated tampon is placed within the constraining walls of packaging materials or a tampon applicator. For the purposes of describing this suggestion, the walls 76 in FIG. 7 may be taken as such constraining walls. It seems then, that for the tampon to "grow" axially, it is necessary for the pleats to unfold and hence for the pleats 78 to rise, in a radial direction away from the cylindrical wall portions 74 of the tampon. It also appears that with little constraining force, the constraining walls 76 preclude this rising of the pleats and hence the axial growth of the tampon is precluded.

The specification above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for axially compressing a cylindrical blank having an insertion end, a withdrawal end, and cylindrical walls therebetween, into a dimensionally stable tampon comprising:

introducing said blank coaxially into a cylindrical compression chamber having a closed insertion end, a withdrawal end and cylindrical walls therebetween wherein the cylindrical walls of said blank make frictional contact with the cylindrical walls of the compression chamber;

axially compressing said blank to about 15 to about 30% of its length prior to compression, said compression being applied to the extent that, through the action of the frictional contact, a plurality of circular pleats are formed around the axially compressed blank, said compression being sufficient to fold said pleats, in the direction of the withdrawal end of the axially compressed blank, to overlie the next adjacent portion of the cylindrical wall of the axially compressed blank.

2. The method of claim 1 wherein the axially compressed blank is allowed to expand after compression to about 50–80% of the length of the blank prior to compression.

* * * * *